United States Patent
Chen et al.

(10) Patent No.: US 8,344,183 B2
(45) Date of Patent: Jan. 1, 2013

(54) METHOD FOR SYNTHESIZING POLYOXYMETHYLENE DIMETHYL ETHERS BY IONIC LIQUID CATALYSIS

(75) Inventors: Jing Chen, Lanzhou (CN); Heyuan Song, Lanzhou (CN); Chungu Xia, Lanzhou (CN); Xinzhi Zhang, Lanzhou (CN); Zhonghua Tang, Lanzhou (CN)

(73) Assignee: Lanzhou Institute of Chemical Physics, Chinese Academy of Sciences, Lanzhou, Gansu Province (CN)

( * ) Notice: Subject to any disclaimer, the term of this patent is extended or adjusted under 35 U.S.C. 154(b) by 534 days.

(21) Appl. No.: 12/548,807

(22) Filed: Aug. 27, 2009

(65) Prior Publication Data

US 2010/0056830 A1 Mar. 4, 2010

(30) Foreign Application Priority Data

Sep. 4, 2008 (CN) .......................... 2008 1 0150868

(51) Int. Cl.
*C07C 41/01* (2006.01)

(52) U.S. Cl. ....................................... 568/594; 568/613
(58) Field of Classification Search ........................ None
See application file for complete search history.

(56) References Cited

U.S. PATENT DOCUMENTS

| | | | |
|---|---|---|---|
| 6,160,174 A | 12/2000 | Hagen et al. | |
| 6,265,528 B1 | 7/2001 | Hagen et al. | |
| 7,208,605 B2 * | 4/2007 | Davis, Jr. | 548/110 |
| 2009/0036715 A1 | 2/2009 | Chen et al. | |

FOREIGN PATENT DOCUMENTS

| | | |
|---|---|---|
| CA | 2 582 502 | 4/2007 |
| CN | 101182367 | 5/2008 |
| EP | 1 505 049 A1 | 2/2005 |
| WO | WO 2006/045506 A1 | 5/2006 |

* cited by examiner

*Primary Examiner* — Rosalynd Keys
(74) *Attorney, Agent, or Firm* — Scully, Scott, Murphy & Presser, P.C.

(57) ABSTRACT

The present invention discloses a method for synthesizing polyoxymethylene dimethyl ethers by ionic liquid catalysis. The method comprises synthesizing polyoxymethylene dimethyl ethers by using a functional acidic ionic liquid as catalyst and using methylal and trioxymethylene as reactant under a relative mild reaction condition. The invention has advantages of high catalyst activity and reaction conversion, simple reaction process, high operationability and controllability, as well as good product distribution and high raw material utilization ratio.

5 Claims, No Drawings

METHOD FOR SYNTHESIZING POLYOXYMETHYLENE DIMETHYL ETHERS BY IONIC LIQUID CATALYSIS

FIELD OF THE INVENTION

The present invention relates to a method for synthesizing polyoxymethylene dimethyl ethers by a reaction or methylal and trioxymethylene which using an ionic liquid as catalyst.

BACKGROUND

In recent years, the demand for diesel oil is increasing gradually in the world. However, the limited diesel oil resource is decreasing gradually, and therefore, a trend of insufficient diesel oil supply and increasing price is occurred. Additionally, because the molecular weight of paraffin in the components of diesel oil is relatively large, the combustion ratio is not high enough, and the combustion performance is not good sufficiently, not only the diesel oil consumption is increased, but also the pollution degree of exhaust to the environment is aggravated. In order to attain an object of energy saving and environmental protection, the research on diesel oil additives in the technological and industrial fields all around the world is enhanced. Polyoxymethylene dimethyl ethers ($RO(CH_2O)_nR$) has very high cetane value and oxygen content (42%-49% for the methyl series and 30%-43% for the ethyl series). The addition of polyoxymethylene dimethyl ethers into diesel oil in an amount of 10%-20% can improve the combustion characteristic of diesel oil prominently, increase the heat efficiency effectively and reduce the discharge of $NO_x$ and microparticles. In view of the vapor pressure, the boiling point and the solubility in oil products thereof, polyoxymethylene dimethyl ethers ($DMM_{3-8}$) with $3 \leq n \leq 8$ is generally used as an oil product additive Polyoxymethylene dimethyl ethers ($DMM_n$) was early synthesized by taking methanol, formaldehyde, polyformaldehyde or glycol ethylidene formal as raw materials under a catalysis of sulfuric acid or hydrochloric acid. In recent years, BASF (WO 2006/045506 A1, CA 2582502) obtained $DMM_{3-8}$ with a content below 26% by reacting at 100° C. for 8-12 h in the case of taking a protonic acid, for example, sulfuric acid, trifluoromethylsulfonic acid or the like, as catalyst and taking methylal and trioxymethylene (or polyformaldehyde) as raw materials. The method has a rigorous reaction condition, a low conversion ratio and a low content of the component which can be used as an oil product additive. In 2005, De Gregori etc. (EP 1505049 A1) synthesized $DMM_{3-8}$ with a reaction under $N_2$ of 1.0 MPa using a protonic acid catalyst. The reaction time was reduced greatly and the $DMM_{3-8}$ yield could be up to 51.2%. The above catalysts have the disadvantages of serious corrosion, difficult separation incapable circulating application, large processing energy consumption, unreasonable product distribution, low trioxymethylene conversion ratio, and low selectivity for the component of $DMM_{3-8}$ which can be used as an oil product additive, and the like. BP (U.S. Pat. No. 6,160,174, U.S. Pat. No. 6,265,528 B1) performed a research on multiphase catalysis and synthesized $DMM_{3-8}$ with a content of only 11.6% in the case of using methanol, formaldehyde, dimethyl ether and methylal as raw materials. Because the method has a low catalyst activity and a complex process, it is difficult to be industrialized. Being a new green solvent or catalyst, ionic liquid has become a hotpoint of the green chemistry research due to the unique advantages of adjustable polarity, wide liquid range, high thermal stability and almost neglectable vapor pressure or the like. Ionic liquid has been widely used in some important aldolisations. In 2007, Lanzhou Institute of Chemical Physics, Chinese Academy of Sciences reported a method for synthesizing $DMM_n$ by a reaction of methanol and trioxymethylene taking an ionic liquid as catalyst, wherein the reaction conversion could be up to 90.3% and the selectivity for $DMM_{3-8}$ could be up to 42.6% (CN 200710018474.9).

DISCLOSURE OF THE INVENTION

An object of the invention is to overcome the disadvantages in the prior art of strong corrosion, difficult separation, incapable circulating application, unreasonable product distribution and the like, and to provide a method for synthesizing polyoxymethylene dimethyl ethers by a reaction of methylal and trioxymethylene which taking an ionic liquid as catalyst under a relatively mild condition.

The reaction formula of the invention is:

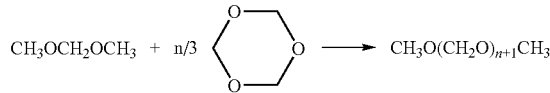

wherein n represents an integer of 1 to 8.

A method for synthesizing polyoxymethylene dimethyl ethers by ionic liquid catalysis, characterized in that the method comprises synthesizing polyoxymethylene dimethyl ethers by taking a functional acidic ionic liquid as catalyst and taking methylal and trioxymethylene as reactants under nitrogen gas atmosphere with a reaction temperature of 95-130° C., a reaction pressure of 0.8-4.0 MPa and a reaction time of 0.5-1 h, wherein the functional acidic ionic liquid has a cation moiety selected from the group consisting of 1-(4-sulfobutyl)-3-methylimidazolium or 1-(methyl 4-butyl-1-sulfonate)-3-methylimidazolium, and an anion moiety selected from the group consisting of hydrosulfate and monomethyl sulfate.

In the above described method, the molar ratio of trioxymethylene to methylal is 0.1-3.0.

In the above described method, the addition amount of the catalyst comprises 0.5-8.0 wt % of the total charging amount.

In the above described method, the preferable reaction temperature is 110-120° C.

In the above described method, the preferable reaction pressure is 1.5-3.0 MPa.

The catalyst is separated after the completion of the reaction. The main impurity in the catalyst phase is water and methylal. The catalyst is circularly used directly or after regeneration. In order to increase the yield of diesel oil additive $DMM_{3-8}$ and the utilization ratio of the reacting raw materials, the catalyst is subjected to separation processes of distillation, filtration or the like to separate the unreacted trioxymethylene, $DMM_n$ with n<3 and n>8, and circularly used.

The invention has the following advantages:

1. The ionic liquid as the catalyst has low corrosion and therefore has no specific demand on the apparatus.

2. The conversion of trioxymethylene and the selectivity of $DMM_{3-8}$ are increased effectively. The conversion of trioxymethylene can be up to 95% and the selectivity of $DMM_{3-8}$ can be up to 53.4%.

3. The catalyst can be recovered and circularly used; after several circulations, the catalyst still maintains relatively high catalytic activity which reduced the cost of catalyst effectively 4. The circulating application of the reacting raw material, the polyoxymethylene dimethyl ethers with n<3 and n>8 are realized and therefore, the utilization ratio of the raw material is high.

The invention has high catalyst activity, high reaction conversion, simple reaction process, easy operation, high controllability, good product distribution and high raw material utilization ratio.

SPECIFIC MODE OF CARRYING OUT THIS INVENTION

The ionic liquid catalysts used in the following examples are illustrated as follows:

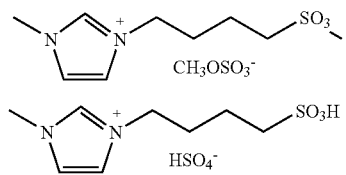

EXAMPLE 1

Into a 1 L reaction kettle, 16.5 g of ionic liquid I, 228.0 g/3.0 mol methylal and 180.0 g/2.0 mol trioxymethylene were added in turn. After the reaction kettle was charged with nitrogen gas to 0.2 MPa, the mixture was stirred and heated to 115° C. in 30 min. At this time, the pressure in the reaction kettle was 1.0 MPa and the reaction time was 40 min. After being cooled, the liquid in the reaction kettle was discharged and kept standing for separation: the upper layer was a colorless transparent reaction liquid; the lower layer was a sticky catalyst phase. The reaction liquid and the catalyst phase were weighed and subjected to gas chromatography analysis. Qualitative and quantitative analysis was conducted with GC/MS (Agilent 7890N/5970C) and GC (Agilent 6820 equipped with a FID detector and SE-54 capillary column), respectively. The TOX conversion was 94.6%. The $DMM_{3-8}$ selectivity was 41.5%.

The catalyst phase was 26.3 g which contained 15.8 g of the ionic liquid, 25.0% of water and 17.1% of impurity of methanol or the like.

EXAMPLE 2

In a testing method which was the same as that in example 1, the catalyst phase was added into a reaction kettle and circularly used, and 0.7 g of a fresh ionic liquid I was supplied each time. After the reaction, the liquid products and the catalyst phase were weighed and subjected to gas chromatography analysis. Qualitative and quantitative analysis was conducted with GC/MS (Agilent 7890N/5970C) and GC (Agilent 6820 equipped with a FID detector and SE-54 capillary column), respectively. Operation conditions and testing results were shown in Table 1.

TABLE 1

Life and activity of catalyst I (ionic liquid I) during circulating application

| Catalyst circulation | Reaction condition | TOX conversion/% | $DMM_{3-8}$ selectivity/% |
|---|---|---|---|
| $R_0$ | 115 ± 1° C./1.0-1.5 MPa/40 min | 94.8 | 39.3 |
| $R_1$ | 115 ± 1° C./1.0-1.5 MPa/40 min | 90.6 | 33.7 |
| $R_2$ | 115 ± 1° C./1.0-1.5 MPa/40 min | 95.1 | 40.3 |
| $R_3$ | 115 ± 1° C./1.0-1.5 MPa/40 min | 95.2 | 41.3 |
| $R_4$ | 115 ± 1° C./1.0-1.5 MPa/40 min | 94.0 | 48.9 |
| $R_5$ | 115 ± 1° C./1.0-1.5 MPa/40 min | 94.0 | 40.5 |
| $R_6$ | 115 ± 1° C./1.0-1.5 MPa/40 min | 92.8 | 44.4 |
| $R_7$ | 115 ± 1° C./1.0-1.5 MPa/40 min | 94.3 | 43.6 |
| $R_8$ | 115 ± 1° C./1.0-1.5 MPa/40 min | 94.2 | 41.9 |
| $R_9$ | 115 ± 1° C./1.0-1.5 MPa/40 min | 95.8 | 40.8 |

EXAMPLE 3

Example 3 was performed in the same method as that in example 1 except that the catalyst was the ionic liquid II, the addition amount of methylal was 167.2 g/2.2 mol, the addition amount of trioxymethylene was 180.0 g/2.0 mol, and that the reaction pressure was 2.0 MPa. After the reaction, the liquid products and the catalyst phase were weighed and subjected to gas chromatography analysis. Qualitative and quantitative analysis was conducted with GC/MS (Agilent 7890N/5970C) and GC (Agilent 6820 equipped with a FID detector and SE-54 capillary column), respectively. The TOX conversion ratio was 89.1%. The $DMM_{3-8}$ selectivity was 52.4%.

EXAMPLE 4

In a testing method which was the same as that in example 1, the catalyst phase obtained in example 3 was added into a reaction kettle and circularly used, and 0.7 g of a fresh ionic liquid II was supplied each time. The liquid products and the catalyst phase were weighed and subjected to gas chromatography analysis. Qualitative and quantitative analysis was conducted with GC/MS (Agilent 7890N/5970C) and GC (Agilent 6820 equipped with a FID detector and SE-54 capillary column), respectively. Operation conditions and testing results were shown in Table 2.

TABLE 2

Activity of catalyst II (ionic liquid II) during circulating application

| Catalyst circulation | Reaction condition | TOX conversion ratio/% | $DMM_{3-8}$ selectivity/% |
|---|---|---|---|
| $R_0$ | 115 ± 1° C./1.5-2.0 MPa/40 min | 89.1 | 52.4 |
| $R_1$ | 115 ± 1° C./1.5-2.0 MPa/40 min | 90.6 | 53.4 |
| $R_2$ | 115 ± 1° C./1.5-2.0 MPa/40 min | 91.1 | 51.8 |
| $R_3$ | 115 ± 1° C./1.5-2.0 MPa/40 min | 88.7 | 52.6 |

We claim:

1. A method for synthesizing polyoxymethylene dimethyl ethers by ionic liquid catalysis, characterized in that the method comprises synthesizing polyoxymethylene dimethyl ethers by using a functional acidic ionic liquid as catalyst and using methylal and trioxymethylene as reactants under nitrogen gas atmosphere with a reaction temperature of 95-130° C., a reaction pressure of 0.8-4.0 MPa and a reaction time of 0.5-1 h, wherein the functional acidic ionic liquid has a cation moiety selected from the group consisting of 1-(4-sulfobutyl)-3-methylimidazolium or 1-(methyl 4- butyl-1-sulfonate)-3-methylimidazolium, and an anion moiety selected from the group consisting of hydrosulfate and monomethyl sulfate.

2. The method according to claim 1, characterized in that the molar ratio of trioxymethylene to methylal is 0.1-3.0.

3. The method according to claim 1, characterized in that the addition amount of the catalyst comprises 0.5-8.0 wt % of the total charging amount.

4. The method according to claim 1, characterized in that the reaction temperature is 110-120° C.

5. The method according to claim 1, characterized in that the reaction pressure is 1.5-3.0 MPa.

* * * * *